United States Patent [19]

Tweardy

[11] Patent Number: 5,302,170
[45] Date of Patent: Apr. 12, 1994

[54] EXTERNAL FIXATION SYSTEM FOR THE NECK

[75] Inventor: Lisa A. G. Tweardy, Mt. Laurel, N.J.

[73] Assignee: The Jerome Group, Inc., Moorestown, N.J.

[21] Appl. No.: 963,442

[22] Filed: Oct. 19, 1992

Related U.S. Application Data

[63] Continuation-in-part of Ser. No. 647,228, Jan. 4, 1991, Pat. No. 5,156,588.

[51] Int. Cl.⁵ .................................................. A61F 5/00
[52] U.S. Cl. ........................................ 602/17; 602/18
[58] Field of Search ................ 602/17, 18; 606/54-59

[56] References Cited

U.S. PATENT DOCUMENTS

| 2,225,274 | 12/1940 | MacGoun . | |
|---|---|---|---|
| 2,820,455 | 1/1958 | Hall . | |
| 2,855,202 | 10/1958 | Kinne . | |
| 3,072,118 | 1/1963 | Starderwick et al. | 602/17 |
| 3,604,412 | 9/1971 | Gardner . | |
| 3,654,923 | 4/1972 | Crutchfield . | |
| 3,669,102 | 6/1976 | Harris . | |
| 3,923,046 | 12/1975 | Heifetz . | |
| 4,112,935 | 9/1978 | Latypov et al. | 606/61 X |
| 4,267,830 | 5/1981 | Vick | 602/19 |
| 4,360,028 | 11/1982 | Barbier et al. . | |
| 4,397,307 | 8/1983 | Keller . | |
| 4,444,179 | 4/1984 | Trippi . | |
| 4,541,421 | 9/1985 | Iversen et al. | 602/18 |
| 4,612,930 | 9/1986 | Bremer . | |
| 4,644,943 | 2/1987 | Thompson et al. | 606/64 |
| 4,667,660 | 5/1987 | Eingorn . | |
| 4,735,196 | 4/1988 | Krag et al. . | |
| 4,913,135 | 4/1990 | Mattingly | 602/18 |
| 5,010,881 | 4/1991 | Boudreau et al. . | |
| 5,062,415 | 11/1991 | Weatherby et al. . | |
| 5,063,920 | 11/1991 | Moore . | |
| 5,088,482 | 2/1992 | McGuinness | 602/18 |

FOREIGN PATENT DOCUMENTS

| 3302078 | 7/1984 | Fed. Rep. of Germany . |
| 140162 | 12/1960 | U.S.S.R. . |
| 633526 | 11/1978 | U.S.S.R. . |
| 1489760 | 6/1989 | U.S.S.R. . |
| 1503797 | 8/1989 | U.S.S.R. . |

OTHER PUBLICATIONS

Durr-Fillauer Medical, Inc. Advertisements Exact date unknown, Believed to be prior to Jan. 4, 1991.
Kirschner Orthopedic Appliances Advertisements Exact date unknown, Believed to be prior to Jan. 4, 1991.
Bremer Orthopedics Advertisements Exact date unknown, Believed to be prior to Jan. 4, 1991.
Ace Medical Company Advertisements Eact date unknown, Believed to be prior to Jan 4, 1991.
Levtech Promotion Materials, 1986.
Progress Mankind Technology (PMT) Corporation Advertisements from 1986-1988.
Ace Orthopedia Company Advertisement, Jun. 1973.

Primary Examiner—Richard J. Apley
Assistant Examiner—Linda C. M. Dvorak
Attorney, Agent, or Firm—Ratner & Prestia

[57] ABSTRACT

A device is provided for maintaining the head of a patient in predetermined spatial relationship to the body of the patient. The device comprises an truncated elliptical member (halo) adapted to fit around the patient's head from front to back. The device also includes a superstructure for attaching the open-backed halo to a vest worn by the patient. The superstructure includes both horizontal and vertical rack and pinion adjustments for adjusting the height and angulation of the halo.

15 Claims, 13 Drawing Sheets

EXTERNAL FIXATION SYSTEM FOR THE NECK

CROSS REFERENCE TO RELATED APPLICATIONS

This application is a continuation-in-part of U.S. patent application Ser. No. 647,228 filed Jan. 4, 1991, now U.S. Pat. No. 5,156,588 issued Oct. 20, 1992.

FIELD OF THE INVENTION

This invention relates to a medical apparatus for securing a patient's head in a rigid spatial relationship to the patient's body, useful in the treatment of fractures of the cervical spine.

BACKGROUND OF THE INVENTION

There are applications in orthopedic surgery, neurosurgery, and other medical treatments and operative procedures where a patient's head must be engaged and held in a predetermined position with respect to the patient's body. Very often, during healing of injuries involving fracture or dislocation of the cervical spine, a patient's head must be immobilized with respect to the patient's body in order to allow the fractured or dislocated bones to heal. For this purpose, halo traction units have been developed.

A halo traction unit comprises a halo, which rings the patient's head, a superstructure, and a vest, to which the superstructure is secured. The ring halo is held rigidly to the patient's head by "skull pins" which project through threaded holes in the halo and into the patient's skull. Thus the ring halo is held rigidly to the patient's head. The ring halo is then secured to the superstructure which in turn is secured to a vest which the patient wears on his or her chest. This structure maintains the head in a rigid, fixed relationship to the body.

While the patient's head is immobilized, it may be desirable to subject the patient to a magnetic resonance imaging machine (MRI, or NMR) or conventional x-rays, CAT scan, or other radiographic imaging tests. Therefore, it is desirable that the material for a halo be non-magnetic, and radio transparent, or at least that the material not interfere significantly with such tests.

When a patient initially enters a hospital directly from an accident scene, very often he or she will be strapped to a backboard or other head and neck immobilizing device. Based upon diagnostic results it may be desirable to attach a halo or skull tongs to provide traction and/or to immobilize the head and neck without moving the patient until the treatment has been applied. Many prior art halos are circular, and completely encircle the head of the patient. This makes impossible the application of the halo to the patient without removal of the patient from the backboard. Therefore, the patient's head must be moved or extended over the edge of the backboard or bed.

Recently, halos have been developed which have open backs, and which, therefore, allow application to the patient while the patient remains on a backboard or bed. However, due to the materials of construction and particular configurations of such open-backed halos, the open-backed halos are not extremely rigid. This instability is caused by removal of the back portion of the halo. As a result, the halo flexes when applied to and worn by the patient. This flexing results in movement of the skull pins against the skull and possible loosening of the skull pins. Such movement results in infections and other associated problems and should be eliminated. Preferably, one step toward elimination of these problems would be development of an open-backed halo with high rigidity.

Movement and loosening of skull pins is also caused by vibrations transmitted from the vest to the halo and patient's head through the superstructure and skull pins of the halo. The vibrations are caused simply by walking or other common movement. The transmission of these vibrations should also be reduced or eliminated to lessen the possibility of loosening of the skull pins.

If a patient is subjected to traction using skull tongs, prior art ring halos and open-backed halos require that the skull tongs be removed prior to application of the halo. It is undesirable to remove a patient from traction in this manner, and thus it would be preferable to apply a halo without removal of the skull tongs. This has heretofore been impossible.

Once a patient has been fitted with a halo, the halo is attached to a superstructure and vest worn by the patient, as previously explained. Generally, such attachment is accomplished by four vertical posts which run directly from the halo to a vest unit. Drawbacks with such a system include difficulty of adjusting of four separate posts to obtain even tension on the posts, and to obtain the correct position of the patient's head with respect to the patient's body. Further, such a unit is somewhat unnerving and distressing to patients. A superstructure which would provide simple adjustment without bulkiness would therefore be desirable.

SUMMARY OF THE INVENTION

The present invention comprises a device for maintaining the head of a patient in predetermined spatial relationship to the body of the patient. The device comprises an elliptical member (halo) adapted to fit around the patient's head from front to back. The elliptical member is truncated at the back (open-backed), and in one embodiment includes downwardly projecting segments adjacent the truncated portion. The elliptical member, or open-backed halo may include a stiffening brim integrally associated with it at the front portion of the halo. Alternatively, the halo may be compression molded with integral carbon fibers which would result in lightweight and high rigidity. The halo also includes a plurality of mounting holes for receiving skull pins to contact and grip the patient's head. Further, midway between the front of the elliptical member (open-backed halo) and the rear of the elliptical member are located two depressed segments. Each depressed segment allows for positioning of skull tongs on the patient's head, thus allowing application of the halo while the skull tongs remain on the patient. The device also includes adjustable means for attaching the open-backed halo to a vest worn by the patient. The adjustable means comprises two elongated vertical extensions which attach to the depressed sections of the open-backed halo or elliptical member, and to a connect. This connect is attached to a T-bar which is attached to a vertical member secured ultimately to the vest. The T-bar, vertical member and extension provide one horizontal and two vertical adjustments. A ball and socket between the extension and halo allows adjustment of the angulation of the halo. This combination provides simple adjustment and positioning of the head of the patient. The skull pins of the present invention are equipped with vibrational isolators to reduce transmission of vibrations from the halo, vest, and superstructure to the skull pins, thereby reducing pin loosening and accompanying complications.

DETAILED DESCRIPTION OF THE DRAWINGS

Figure 1:
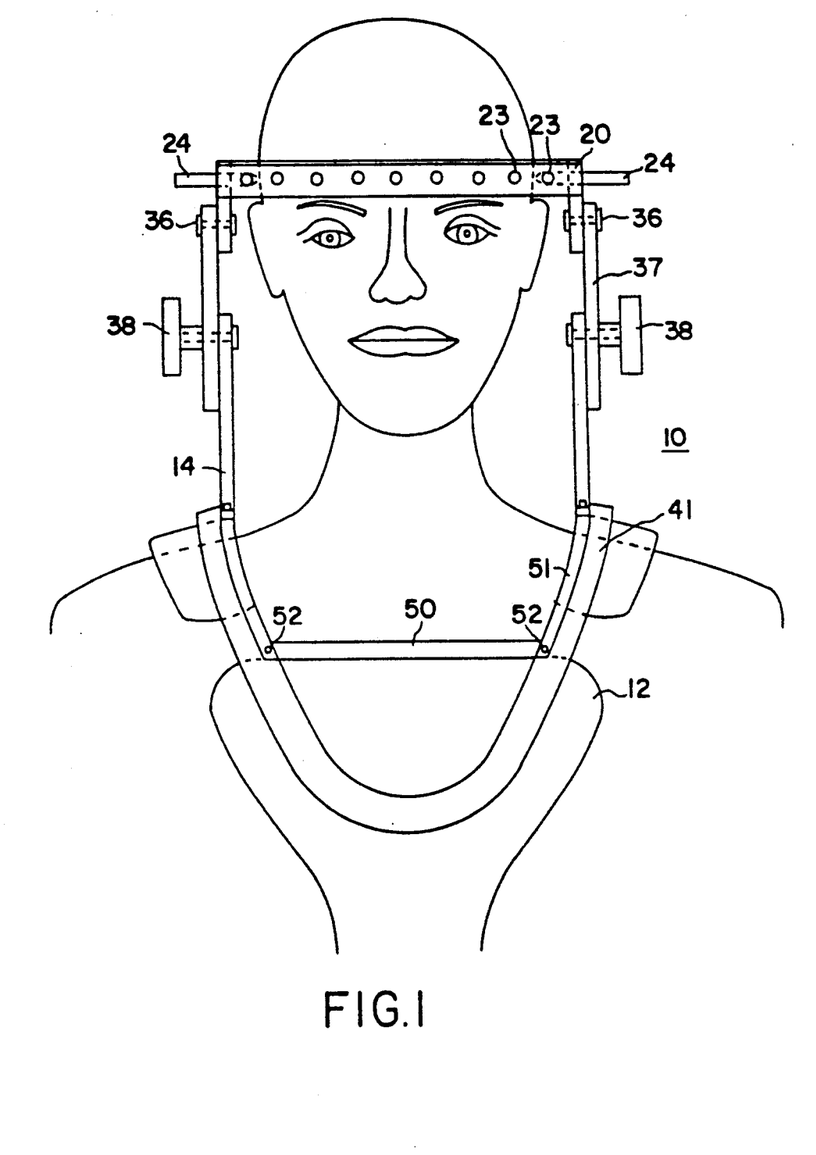
FIG. 1 is a front view of a first embodiment of the device of the present invention when fitted to a wearer.

Referring now to FIG. I, head immobilizing device 10 comprises generally halo, or elliptical member, 20, and means for rigidly attaching the halo to the patient's body, comprising generally a vest 12 and a superstructure 14. It should be noted that the left and right sides of superstructure 14 are mirror images of one another. This is also true for superstructure 114. The component 20 of the present invention will be referred to here as a "halo" which is the term commonly used by those skilled in the art, or "elliptical member" which defines the component in terms of its shape. It should be understood that these terms are being used interchangeably.

Figure 2:
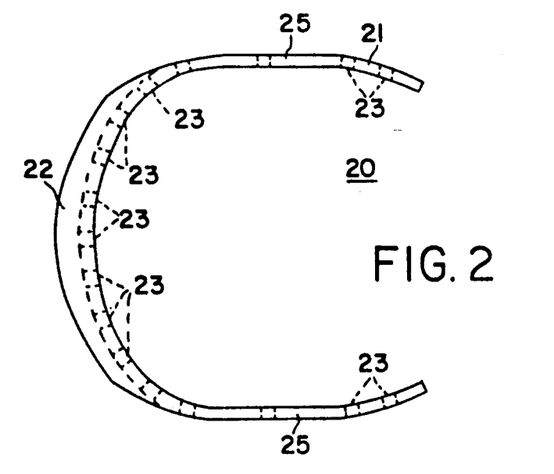
FIG. 2 is a top view of a first embodiment of the halo of the device of the present invention.
Figure 3:
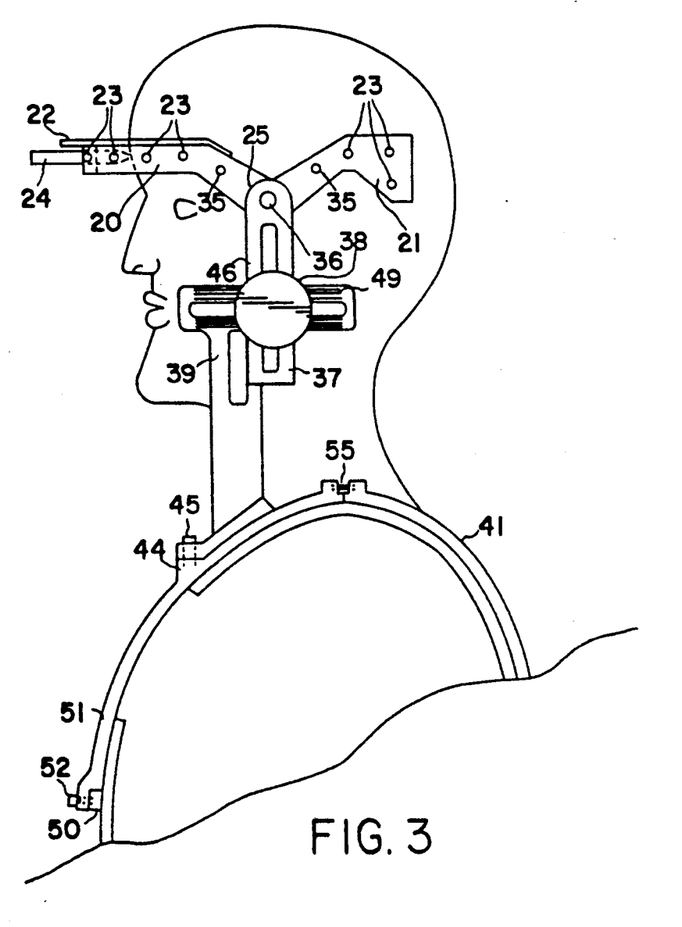
FIG. 3 is a side view of a first embodiment of the device of the present invention when fitted to a wearer.

The particular configuration of the halo 20 can be more easily seen from FIGS. 2 and 3. Halo 20 is a truncated elliptical member as may be seen from FIG. 2. When applied to a patient, as shown in FIG. 3, the halo encircles the patient's head horizontally, just above the ears and eyebrows of the patient. This area may be referred to as the "equator" of the patient's head, or as a capital-distal plane. The halo is truncated, so the back thereof is removed and open. As used herein, the "back" or "front" of the halo refer to the portions of the halo at the posterior and anterior of the patient respectively when the halo is applied as shown in FIG. 3. The truncation allows the halo to be applied to a person secured to a backboard or lying supine in a bed, without removal of the patient's head from the backboard or bed surface. Adjacent the truncated section of the halo are two downwardly projecting segments 21, which extend out of the plane of the major portion of the halo. The extension of these sections allows one to obtain a more secure grip on the head of the patient by placing the skull pins below the capital-distal plane where optimum bone purchase is achieved. Of course, a halo in which these segments 21 were not extended could also be used, but the halo with segments 21 extended downwardly is preferred.

Figure 5:
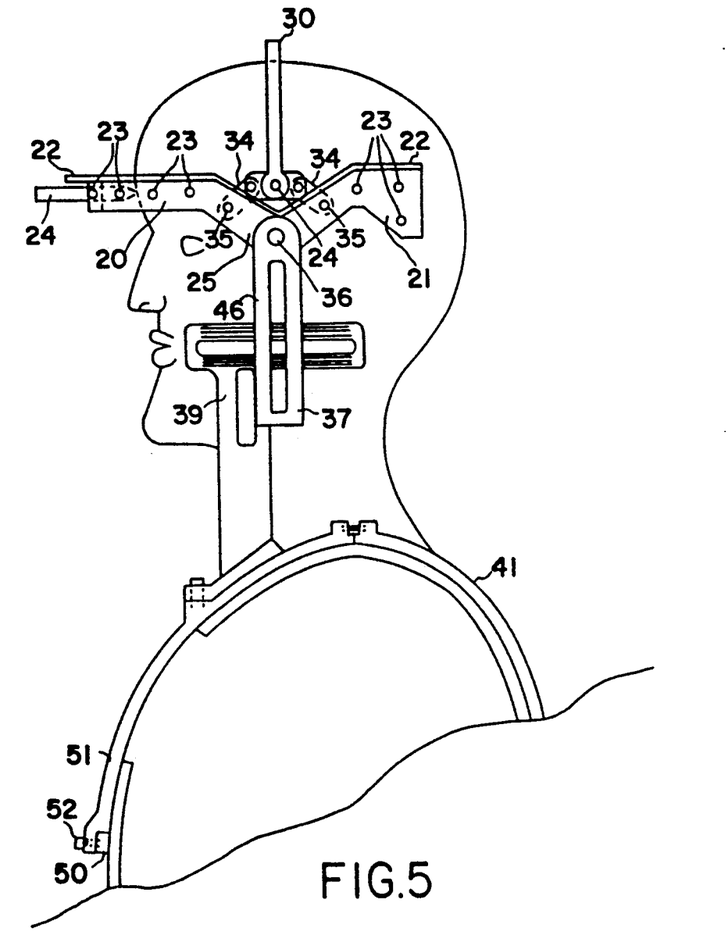
FIG. 5 is a side plan view of a first embodiment of the device of the present invention when fitted to a wearer showing placement of skull tongs.

As previously mentioned, structural rigidity of halo 20 is a major concern in avoiding skull pin complications. Therefore halo 20 also includes a stiffening brim 22 integrally associated therewith. The brim is generally a flat, arcuate piece of material and may be made from the same material of construction as the remainder of the curved halo 20. Brim 22 may be made separately from the remainder of halo 20, in which case the brim should be welded, or permanently attached by other means to halo 20. If made separately, brim 22 can be made from a different material from halo 20. Brim 22 may also be made integrally with the remainder of halo 20 as a one-piece, molded or formed unit. The brim adds rigidity and flexural stability to halo 20, and this allows the integrity of the ring to be broken and the skull pins to be securely fastened to the patient's head without movement or flexing of halo 20, which would otherwise cause the skull pins to move, leading to infection and associated problems. Brim 22 is located in the front of halo 20, but may also extend over the entire length of halo 20 as shown in FIG. 5.

An alternative configuration of the halo (halo 120) may be seen from FIGS. 9-12. In this configuration, halo 120 has no brim and no downwardly projecting segments adjacent the truncated end, unlike the first embodiment halo 20. However, by choosing a material which has reduced interference with x-rays or other electromagnetic diagnostic tools, the increases thickness will not prevent proper diagnosis of the patient. Accordingly, the halo 120 is constructed by compression molding of a rigid polymer matrix with embedded graphite fibers. This produces a lightweight rigid halo which has very low with electromagnetic imaging techniques.

Halo 20 is provided with a plurality of holes 23 which allow for the use of skull pins 24. The manner for attaching skull pins 24 to halo 20 may be more clearly seen from FIG. 6. Alternative embodiment halo 120 also includes holes 123 for securing skull pins 24 as shown in FIGS. 9-12.

As previously mentioned, it is desirable to reduce transmission of vibrations from halo 20 (or 120) and the superstructure and vest, to the skull pins 24 which are generally formed from a non-magnetic alloy such as a titanium alloy. Such vibrations may cause loosening of skull pins 24. This leads to movement of the skull pins on the patient's head. This can cause the patient's skull to wear down in those places where the skull pins are located. Then, even after tightening, skull pins 24 cannot grip the patient's head securely. Further, movement of skull pins 24 can lead to infection where the pins enter the patient's skin.

Figure 6:
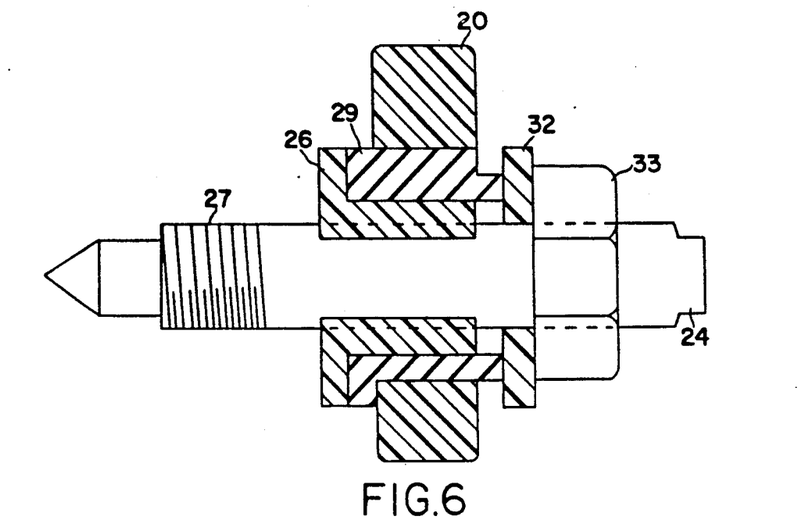
FIG. 6 is a cross-sectional view of a skull pin and accompanying vibrational isolator of the present invention, taken along line 6—6 of FIG. 7.
Figure 7:
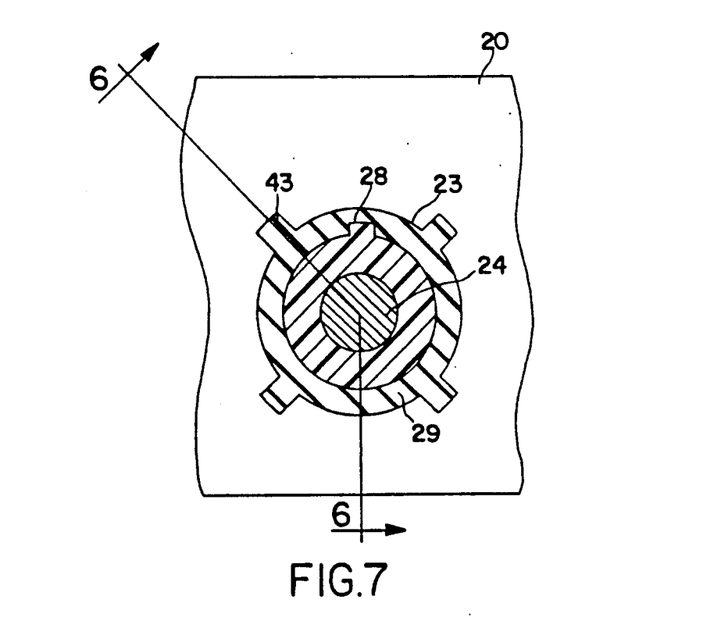
FIG. 7 is a cross-sectional view of a skull pin and accompanying vibrational isolator of the present invention.

FIG. 6 shows skull pin 24 which screws into molded nut 26 thru threads 27. Molded nut 26 is held in rubber isolation mount 29 which, in turn, is fitted in one of the mounting holes 23. Molded nut 26 has a key 28 to prevent rotation of nut 26 with respect to isolation mount 29. Isolation mount 29 also includes keys 43 to prevent rotation with respect to halos 20 and 120. Isolation mount 29 may be made from any suitable elastomeric material and is preferably made from hard rubber which has a high durometer. Once skull pin 24 has been secured in molded nut 26, fiber washer 32 and nut 33 lock the skull pin in the predetermined position and lock the entire vibration isolating assembly to halo 20 or 120 through mounting hole 23. Molded nut 26, fiber washer 32, and nut 33 may all be made from the same material, such as a polymeric resin, a carbon or glass fiber reinforced resin, or a non-magnetic metal alloy. Preferably, a long glass fiber reinforced nylon composite such as Verton from LNP Engineering Plastics in Exton, Pa. may be used for halo 20.

Like halo 20, molded nut 26, fiber washer 32, and nut 33 should not be made from a magnetic material so that the patient can be subjected to magnetic resonance imaging or similar diagnostic procedures. A polyether sulfone also from LNP Engineering Plastics in Exton, Pa. is recommended. These considerations also apply to halo 120. As previously explained, a compression molded graphite reinforced composite is thus preferred for the construction of halo 120.

The entire vibration isolation assembly, comprising molded nut 26, rubber isolation mount 29, fiber washer 32, and nut 33, is held in halo 20 through mounting hole 23 and serves to hold halo 20 rigidly to the patient's head while preventing transmission of vibrations from the patient's vest, superstructure, and halo, to skull pins 24. Skull pins 24 are therefore less likely to loosen or move, and associated complications are reduced. Furthermore, this vibrational isolation assembly can be used throughout the superstructure.

As shown in FIGS. 2 through 5 and 9 through 12, halos 20 and 120 also includes depressed segments 25 and 125 respectively on either side of the halos, located approximately midway between the front of the halo where the brim is located on halo 20 and the back of the halo which has been truncated. The depressed segments 25 provide a number of advantages. As may be seen from FIGS. 4 and 5, depressed segments 25 and 125 allow skull tongs 30 to remain in position on the patient's head while halo 20 is applied. Generally, skull tongs are used for applying traction to a patient in the supine position. The skull tongs are generally applied on the equatorial (or capital distal) plane of the patient's head. As previously explained, this is the same position in which a halo is normally applied. Therefore prior art halos could not be applied to a patient when skull tongs were in place. This meant that a patient had to be removed from traction to apply the halo. Further, with a prior art halo in place, the skull tongs could not be reapplied and the patient could not be placed under traction except that supplied to the halo ring itself by some external means or by the vest, superstructure, and halo.

Depressed segments 25 and 125 allow for attachment of skull tongs 30 while halo 20 or 120 is secured to the patient, or alternatively, allows halo 20 or 120 to be positioned while skull tongs 30 remain in place. The open back of halo 20 or 120 enables the halo to be manipulated around skull tongs 30 or a cable attached thereto for supplying traction. The patient can therefore be subjected to traction without a vest while the halo is in place. Skull tongs 30 can be secured directly to halo 20, as may be seen in FIG. 5. Halo 120 also provides for attachment of skull tongs 30. Skull tongs 30 are equipped with flanges 34. The flanges attach to the skull tongs 30 and to holes 35 in halo 20 and holes 104 in halo 120. These holes may be threaded to accommodate a fastener or a nut may be used with the fastener. Depressed segment 25 allows proper placement of the skull tongs 30 with skull pin 24 in the equatorial plane of the patient's head.

Figure 4:
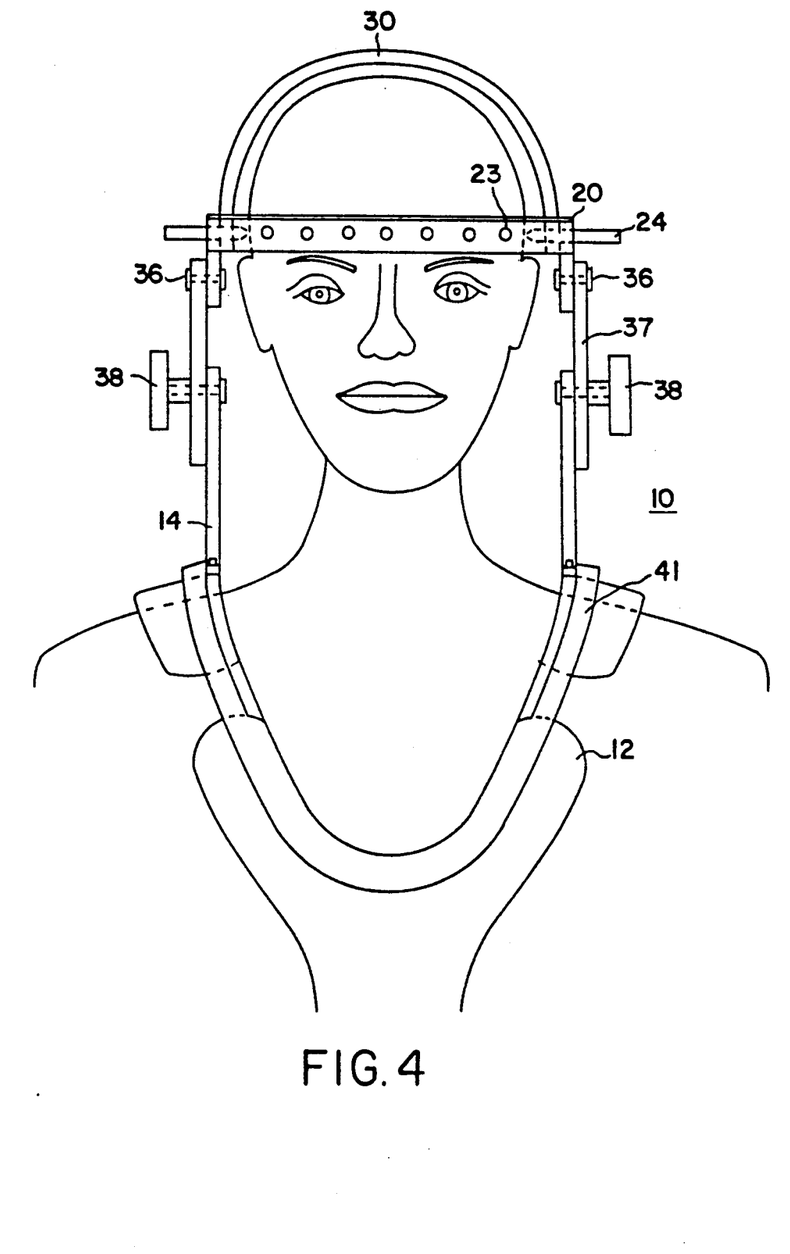
FIG. 4 is a front view of a first embodiment of the device of the present invention when fitted to a wearer showing placement of skull tongs.
Figure 8:
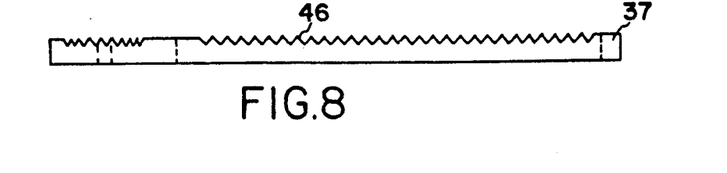
FIG. 8 is a side view of a vertical height adjuster of a first embodiment of the device of the present invention.

Depressed segments 25 also provide for attachment of halo 20 to supporting superstructure 14 as shown in FIGS. 3-5. Halo 20 attaches to vertical height adjuster 37 through lock screw 36. Vertical height adjuster is in turn secured to vertical support 39. Vertical height adjuster 37 and vertical support 39 are equipped with V-grooves 46 and 49 respectively. Vertical height adjuster 37 and vertical support 39 are arranged such that the V-grooves interlock and thus hold the halo securely. Vertical height adjuster 37 can be more easily seen in FIG. 8. V-grooves 46 are adapted to interlock with V-grooves 49 on vertical support 39.

Vertical height adjuster 37 also has V-grooves which interlock with V-grooves on halo 20. These V-grooves grooves on vertical height adjuster 37 and halo 20 cannot be seen from the Figures since superstructure 14 is shown assembled mounted on a patient. Vertical support 39 is attached to over shoulder bar 41, by means of flange 44 on over shoulder bar 41. Vertical support 39 and flange 44 each have V-grooves which interlock. By loosening lock screw 45 rotation about the screw is possible to obtain rotational adjustment of the halo 20. As may be seen from FIGS. 3 and 5, over the shoulder bars are hinged at ball and socket joint 55 to allow rotation around the patient, so that they may be applied while a patient is supine in bed. Vertical height adjuster 37 and vertical support 39 with interlocking V-grooves are held securely together by means of lock knob 38. Lock knob is knurled and can be hand tightened and adjusted to facilitate adjustment of the height of superstructure 14 and halo 20. Lock knob 38 also includes an allen-type (hex socket) locking screw for locking the knob when suitable adjustments have been made. All parts of superstructure 14 are preferably made from the same or similar material to that used for halo 20 since superstructure should also be nonmagnetic and should not allow artifact during diagnostic imaging.

Lateral adjustment of halo 20 and superstructure 14 may be made by means of lateral lock nut 52, as shown in FIGS. 1, 3, and 5. Chest bar 50 connects the two sides of superstructure 14 and front brace 51 connects thereto. Front brace 51 comprises the front portion of over shoulder bar 41. Front brace 51 has V-grooves where it connects to chest bar 50. This allows simple adjustment and securing of the superstructure.

As has been detailed previously, halo 120 is very similar to halo 20 in many ways. Every consideration taken into account in making halo 20 was incorporated into halo 120, excepting brim 22, and therefore all skull pins, skull tongs, vibrational isolators, and keys will also fit halo 120. The only other difference between halo 20 and halo 120 is that halo 120 has been expanded slightly in the region of depressed segments 125 in order to allow more room to accommodate the ears of the patient.

Figure 9:
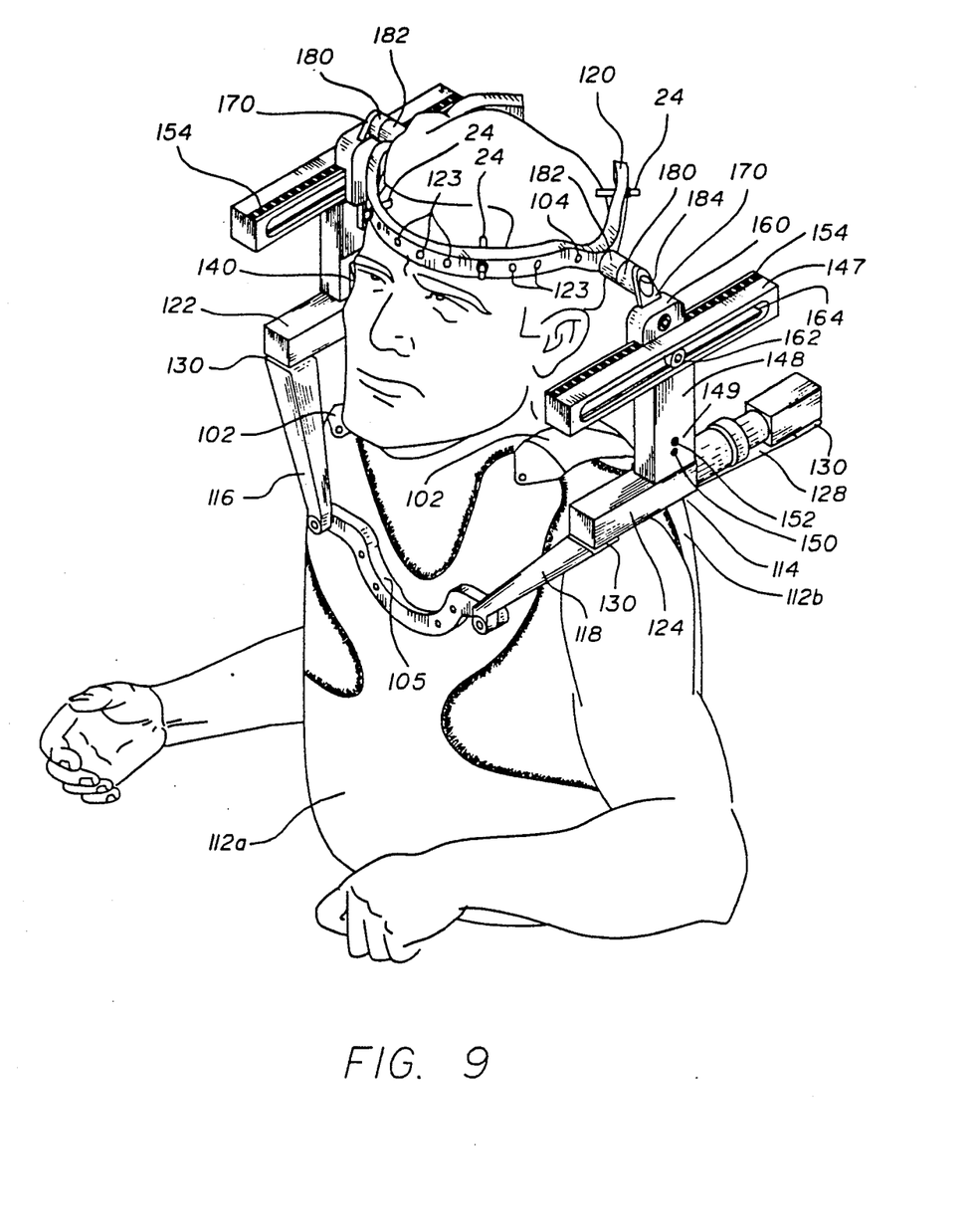
FIG. 9 is a perspective view of a second embodiment of the device of the present invention when fitted to a wearer.
Figure 10:
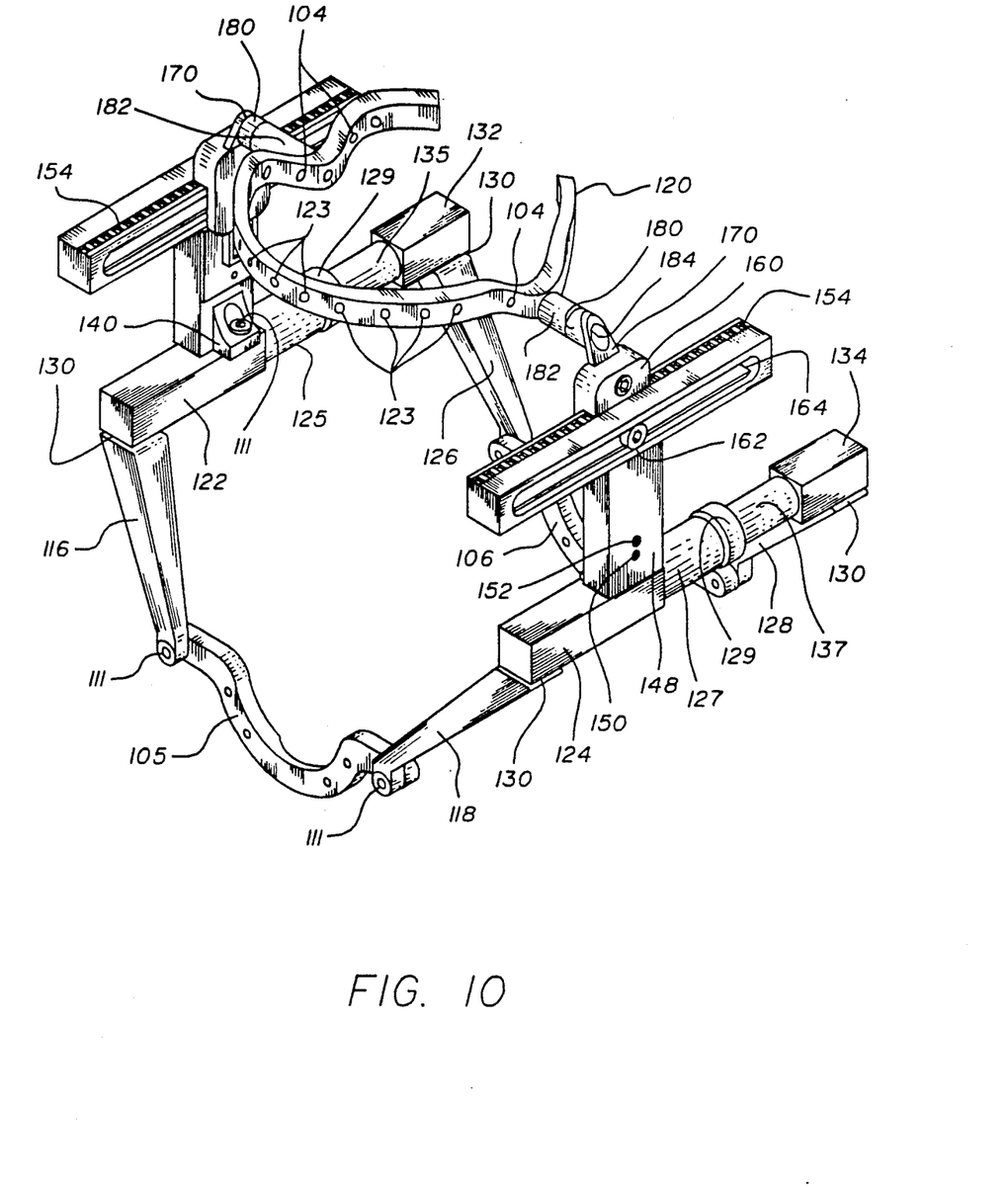
FIG. 10 is a perspective view of a second embodiment of the device of the present invention.
Figure 11:
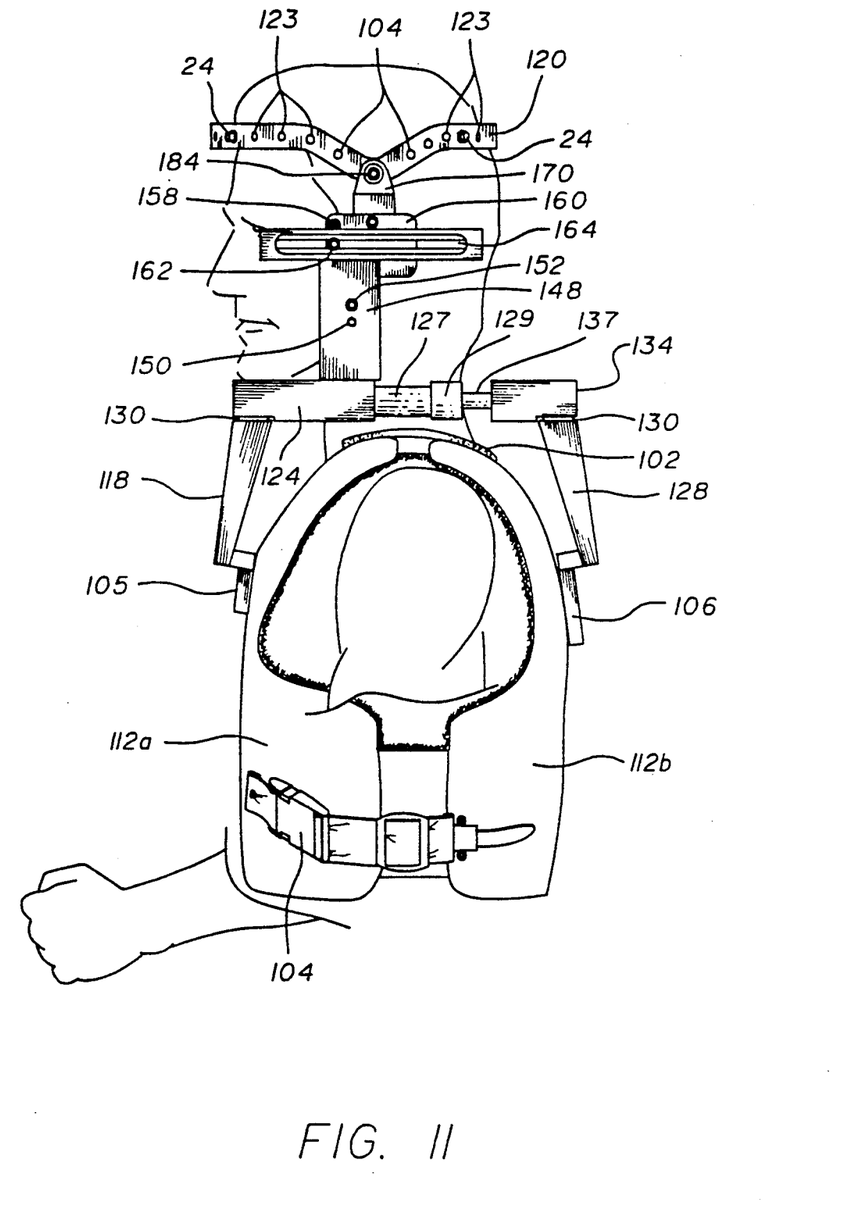
FIG. 11 is a side view of a second embodiment of the device of the present invention when fitted to a wearer.
Figure 12:
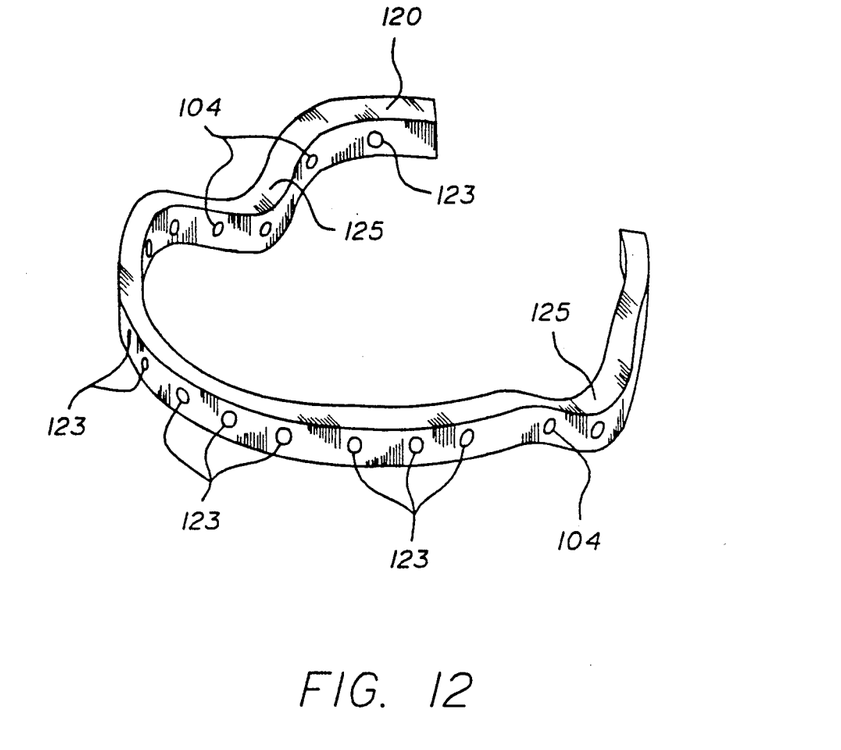
FIG. 12 is a perspective view of a second embodiment of the halo of the present invention.

Although halo 120 is very similar to halo 20, superstructure 114 is very different from superstructure 14, as may be seen from FIGS. 9-11. Superstructure 114 holds the head of a patient in a fixed relationship to the body of the patient. Therefore rigid attachment to both the body and head of the patient is necessary. Superstructure 114 attaches to the body of the patient by means of a vest consisting of front vest portion 112a and rear vest portion 112b. The vest is attached to the patient's body by hook and loop shoulder straps 102 and side buckles 104.

Superstructure 114 is attached to front vest portion 112a and rear vest portion 112b via front brace 105 and rear brace 106 respectively. To front brace 105 is secured front right upright 116 and front left upright 118 (right and left taken as the patient's right and left). Likewise, secured to rear brace 106 is secured rear right upright 126 and rear left upright 128. Uprights 116, 118, 126, and 128 are secured to braces 105 and 106 by any conventional means. Threaded fasteners are preferred since they allow loosening and retightening for adjustment. Particularly, hex cap threaded fasteners 111 which are knurled on the outside of the head while receiving an internal hex key are preferred. In this way, one hex key can be used for all fasteners and adjustments herein.

Uprights 116 and 118 are in turn secured to front right top 122 and front left top 124 respectively through ball and socket joints 130 (where the ball and socket are attached to the upright and top respectively). Uprights 126 and 128 are similarly secured to rear right top 132 and rear left top 134 respectively Ball and socket joint 120 may also include an o-ring situated within the joint to prevent transmission of vibrations from vest portions 112a and 112b to superstructure 114. Front tops 122 and 124 include right and left female pieces 125 and 127 respectively, each having a collet 129 thereon. Right and left female pieces 125 and 127 accept right and left male pieces 135 and 137 respectively. Male pieces 135 and 137 slide in and out of female pieces 125 and 127 and can be locked in place by collets 129. The allows for the continuously variable adjustment of the front to back thickness of the superstructure 114.

Figure 13:
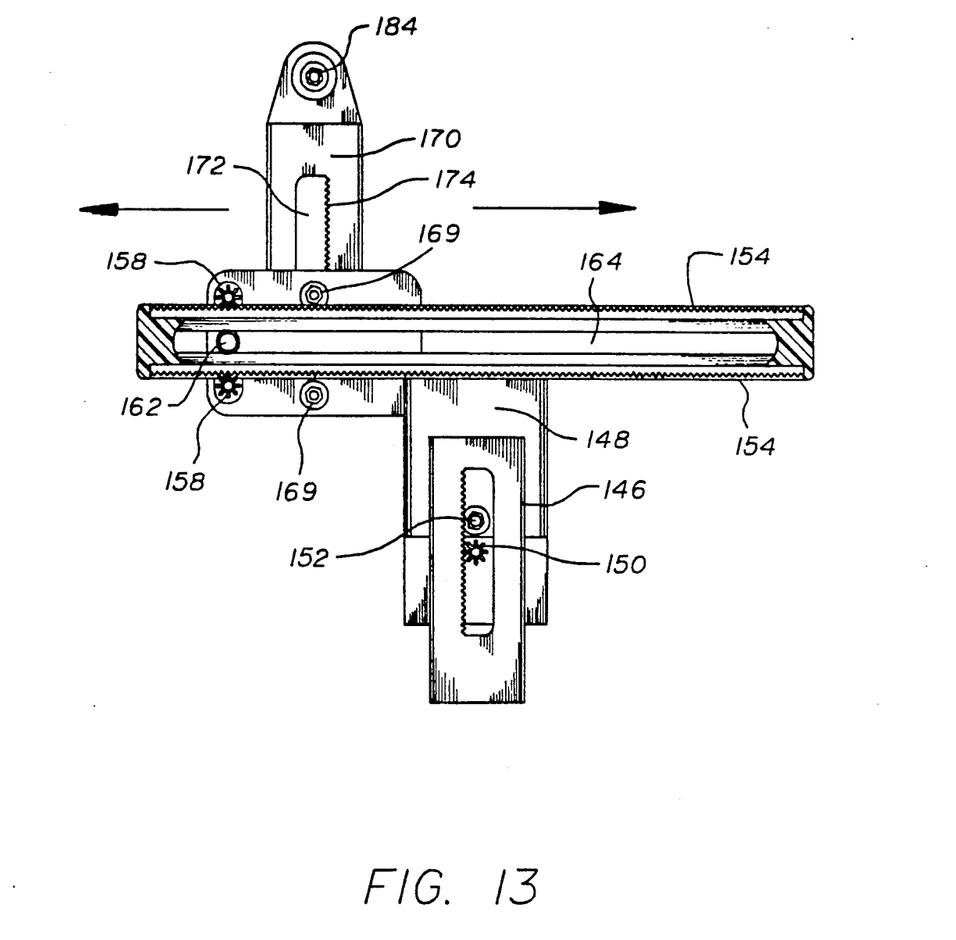
FIG. 13 is a partial cross-sectional view of the vertical and lateral height adjuster of a second embodiment of the device of the present invention.
Figure 14:
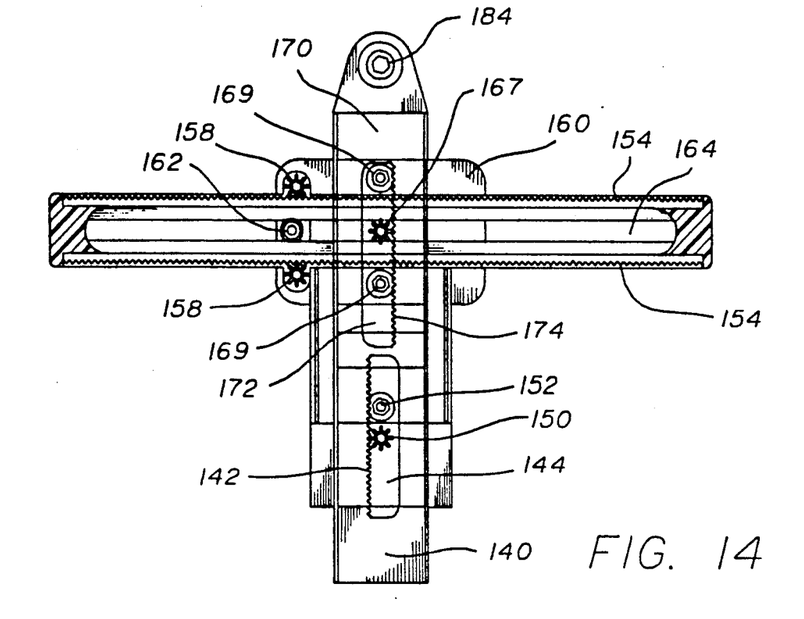
FIG. 14 is a partial cross-sectional view of the vertical and lateral height adjuster of a second embodiment of the device of the present invention.
Figure 15:
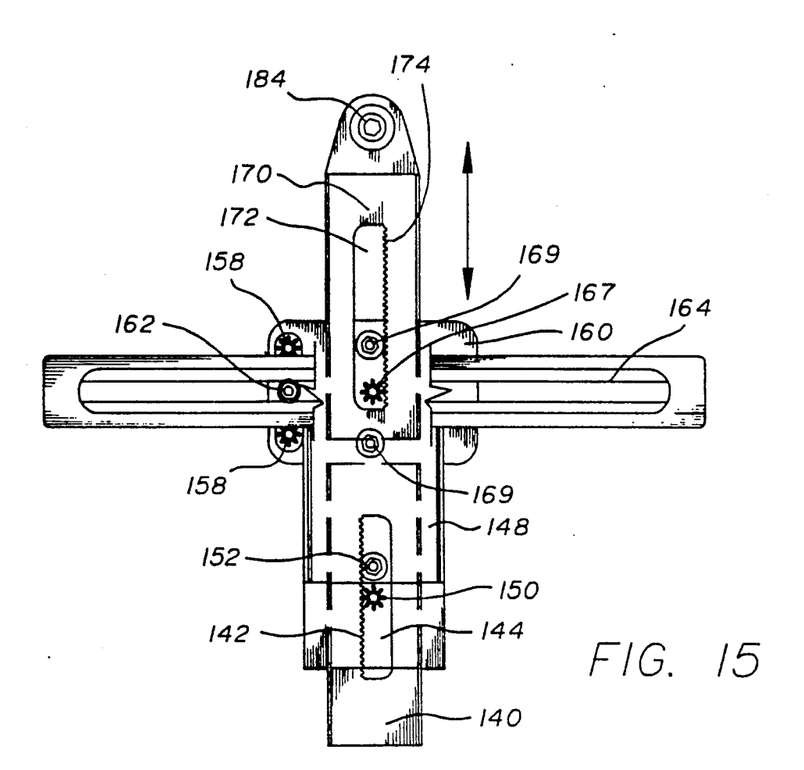
FIG. 15 is a partial cross-sectional view of the vertical and lateral height adjuster of a second embodiment of the device of the present invention.
Figure 16:
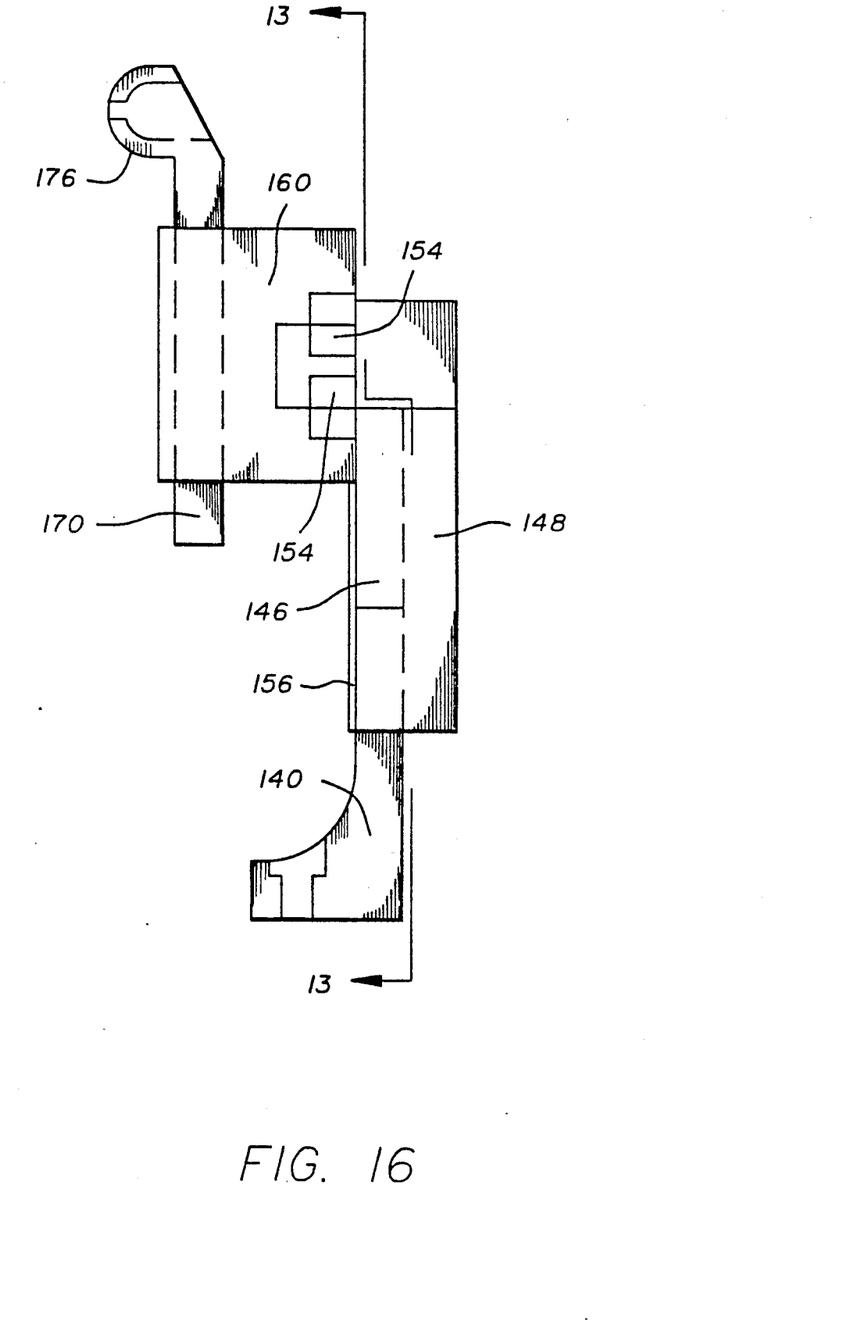
FIG. 16 is a partial side view of the superstructure of the device of the present invention.

Secured to front tops 122 and 124 are vertical pieces 140. Vertical pieces 140 are secured with threaded hex cap fasteners 111. Vertical pieces 140 can be more easily seen in FIGS. 13, 14, and 15. Vertical piece 140 includes rack 142 running vertically along the inside of a channel 144 cut through vertical piece 140. Vertical piece 140 fits into a channel 146 in a T-bar 148. T-bar 148 has a horizontal section 147 and a vertical stem 149. T-bar 148 also includes pinion gear 150 which mates with rack 142. Pinion gear 150 has a hexagonal opening in the center thereof of the same size as the hexagonal openings in threaded hex cap fasteners 111. A threaded hex cap fastener functions as a set screw 152. Set screw 152 engages between T-bar cover 156 and T-bar 148. When set screw 152 is loosened, the key for the fastener can be inserted into pinion gear 150 and turned. This rotation of pinion gear 150 provides continuous adjustment of T-bar 148 with respect to vertical piece 140. This adjusts the height of superstructure 114.

T-bar 148 has two racks 154. These racks interact with gears 158 on connector 160. Rotation of gears 158 provides anterior to posterior adjustability of connector 160 with respect to T-bar 148. This in turn provides anterior to posterior adjustability of halo 120 with respect to vest portions 112a and 112b and thus with respect to the body of the patient. Connector 160 also includes hex cap set screw 162 which extends through channel 164 in T-bar 148 and which can be tightened once the correct anterior to posterior position of halo 120 has been achieved.

Figure 17:
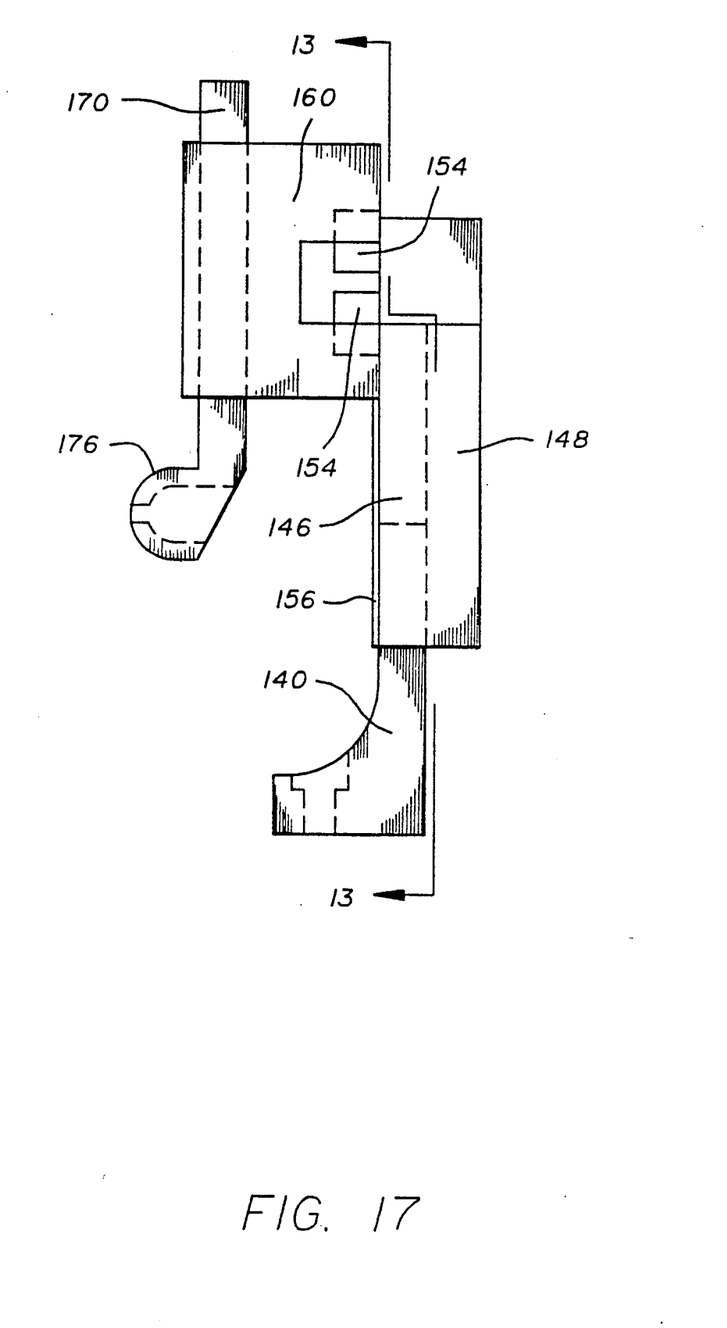
FIG. 17 is a partial side view of the superstructure of the device of the present invention with the extension reversed.

To provide for even greater flexibility in the height of superstructure 114, extension 170 is secured to connect 160. Extension 170 includes a channel 172 therethrough and a rack 174 contained within channel 172. Connect 160 includes pinion gear 167 and hex cap set screws 169 which provide movement and locking of extension 170 with respect to connect 160 respectively. Extension 170 also includes a ball 176 to which halo 120 can be indirectly attached. To provide still greater flexibility, extension 170 can be removed and reversed (turned upside down) as shown in FIG. 17. This is necessary to make certain that with the adjustability of T-bar 148 and extension 170, all possible positions of ball 176 can be accessed.

To ball 176 on extension 170 is attached socket 180 and spacer 182. These are secured with a hex cap set screw 184, which passes through socket 180 and spacer 182 and into halo 120. Spacer 182 is optional, and is used when the halo appropriate for the head of the patient is slightly smaller than the width of the right and left portions of superstructure 114. Hex cap set screw 184 is located in cavity 186 in ball 176. Cavity 186 is rounded on the inside to allow for free movement of set screw 184. With ball 176 and socket 180, the patient's head may also be tilted from side to side, and once set screw 184 is tightened, halo 120 and the patient's head will be maintained in this position.

It is understood that various other modifications will be apparent to one skilled in the art without departing from the spirit and scope of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A device for maintaining the head of a patient in a predetermined spatial relationship to the body of the patient, said device comprising:

an elliptical member including a plurality of mounting holes for receiving skull pins; and adjustable means for rigidly attaching said elliptical member to the body of the patient, said adjustable means comprising:

a vest adapted to be worn by the patient including front and rear braces thereon adapted to extend laterally across the chest and back of the patient;

right and left front uprights secured to and projecting upward from said front brace right and left rear uprights secured to and projecting upward from said rear brace;

a right top portion connecting said right front and right rear braces and a left top portion connecting said left front and left rear braces;

right and left vertical pieces secured to said right and left top portions, each said vertical piece having an elongated vertical slot therethrough and a vertically positioned rack;

right and left T-bars connected to and extending vertically from said right and left vertical pieces each said right and left T-bars having a crossbar situated horizontally and a vertical stem extending therefrom, each said vertical stems including a pinion gear which rides on said vertical piece rack and allows vertical movement relative to said vertical piece, and a set screw to lock and prevent said vertical movement, each said horizontal crossbar having an elongated horizontal slot therethrough and a horizontally positioned rack;

right and left connect pieces each having two pinion gears therein, said two pinion gears comprising a T-bar pinion gear which rides on said T-bar crossbar rack and allows horizontal movement relative to said T-bar crossbar, and a set screw to lock and prevent said horizontal movement, and an extension pinion gear;

right and left extensions, each said extension having an elongated vertical slot therethrough and a vertically positioned rack, which rack rides on said extension pinion gear allowing vertical movement thereof, and a set screw to lock and prevent said vertical movement; and means for connecting said elliptical member to said right and left extensions.

2. The device of claim 1 wherein said means for connecting said elliptical member to said extension comprises:

a ball affixed to one end of each said extension; and a socket piece connected between each said ball and said elliptical member.

3. The device of claim 2 wherein said right and left extensions are positioned such that said balls protrude upwards from said right and left connect pieces.

4. The device of claim 3 further including a spacer between each said socket and said elliptical member.

5. The device of claim 2 wherein said right and left extensions are positioned such that said balls protrude downwards from said right and left connect pieces.

6. The device of claim 5 further including a spacer between each said socket and said elliptical member.

7. The device of claim 1 wherein said right and left top portions are variable in length.

8. The device of claim 1 wherein said uprights include balls on the ends thereof and said right and left top portions include sockets for receiving said balls.

9. The device of claim 8 wherein said right and left top portions are variable in length.

10. The device of claim 8 wherein said means for connecting said elliptical member to said extensions comprises:

a ball affixed to one end of each said extension; and a socket located between each said ball and said elliptical member.

11. The device of claim 10 wherein said right and left extensions are positioned such that said balls protrude upwards from said right and left connect pieces.

12. The device of claim 11 further including a spacer between each said socket and said elliptical member.

13. The device of claim 10 wherein said right and left extensions are positioned such that said balls protrude downwards from said right and left connect pieces.

14. The device of claim 13 further including a spacer between each said socket and said elliptical member.

15. The device of claim 10 including an o-ring positioned between said ball and said socket.

* * * * *